(12) United States Patent
Magnani (10) Patent No.: US 7,135,301 B2
(45) Date of Patent: Nov. 14, 2006

(54) DETECTION AND TREATMENT OF PROSTATE CANCER

(75) Inventor: John L. Magnani, Gaithersburg, MD (US)

(73) Assignee: GlycoMimetics, Inc., Gaithersburg, MD (US)

( * ) Notice: Subject to any disclaimer, the term of this patent is extended or adjusted under 35 U.S.C. 154(b) by 358 days.

(21) Appl. No.: 10/176,960

(22) Filed: Jun. 21, 2002

(65) Prior Publication Data

US 2003/0096327 A1 May 22, 2003

Related U.S. Application Data

(60) Provisional application No. 60/300,250, filed on Jun. 21, 2001.

(51) Int. Cl.
*G01N 33/574* (2006.01)
*C07K 16/30* (2006.01)

(52) U.S. Cl. .......................... 435/7.23; 435/7.1; 435/4; 530/388.8

(58) Field of Classification Search .................. 435/7, 435/7.1, 4, 7.23; 514/2; 424/130, 178.1
See application file for complete search history.

(56) References Cited

U.S. PATENT DOCUMENTS 4,863,713 A 9/1989 Goodwin et al. ............. 424/1.1
5,227,160 A * 7/1993 Nudelman et al. ........ 424/137.1

FOREIGN PATENT DOCUMENTS

WO WO 97/03701 2/1997

OTHER PUBLICATIONS

Tsuji et al. J. Exp. Med. 1988,168: 343-356.*
Nudelman et al., J Biol Chem 1989, 264: 18719-18725).*
Fundamental Immunology p. 242,William E. Paul, M.D. ed., 3d ed. 1993.*
Nudelman et al. (JBC 1989; 264: 18719-18725).*
Itai et al., "Differentiation-dependent Expression of 1 and Sialyl 1 Antigens in the Developing Lung of Human Embryos and in Lung Cancers," *Cancer Res.* 50:7603-7611, Dec. 1, 1990.
Nudelman et al., "A Series of Disialogangliosides with Binary 2→3 Sialyllactosamine Structure, Defined by Monoclonal Antibody NUH2, Are Oncodevelopmentally Regulated Antigens," *J.Biol. Chem.* 284(31): 18719-18725, Nov. 5, 1989.
Kannagi et al, "Quantitative and Qualitative Characterization of Human Cancer-associated Serum Glycoprotein Antigens Expressing Fucosyl or Sialyl-Fucosyl Type 2 Chain Polylactosamine," *Cancer Res.* 46:2619-2626, 1986.
Laganà, A. et al., "Determination of serum total lipid and free N-acetylneuraminic acid in genitourinary malignancies by fluorimetric high performance liquid chromatography. Relevance of free N-acetylneuraminic acid as tumour marker," *Clinica Chimica Acta* 243:165-179, 1995.
Satoh, M. et al., "Glycolipid Expression in Prostatic Tissue and Analysis of the Antigen Recognized by Antiprostatic Monoclonal Antibody APG1," *Urol. Int. 48*: 20-24, 1992.
Shiraishi, T. et al., "The glycosphingolipids of human prostate tissue," *Biochimica et Biohphysica Acta 961*: 160-169, 1988.

\* cited by examiner

*Primary Examiner*—Jeffrey Siew
*Assistant Examiner*—Brandon Fetterolf
(74) *Attorney, Agent, or Firm*—Seed IP Law Group PLLC (57) ABSTRACT

An antigen is shown to be associated with prostate cancer, and is useful for new methods and compositions for diagnosing or treating prostate cancer. This is particularly useful for individuals with prostate cancer who test negative for Prostate Specific Antigen. Additionally, this is useful for distinguishing between benign prostate disease and prostate cancer in a patient diagnosed or presenting with prostate dysfunction.

2 Claims, 12 Drawing Sheets

| Tissue | Staining |
|---|---|
| Prostate Adenocarcinoma | Strongly Positive |
| Glandular prostate epithelial layer (single layer) | Strongly Positive |
| Other normal Prostate Tissue | Negative |
| Colon | Negative |
| Duodenum | Negative |
| Spleen | Negative |
| Skeletal Muscle | Negative |
| Smooth Muscle | Negative |
| Stomach | Negative |
| Blood Vessel | Negative |
| Ovarian Cancer | Negative |
| Kidney | Negative (except very light on tubules) |
| Tonsil | Negative (except few scattered single cells) |

DETECTION AND TREATMENT OF PROSTATE CANCER

CROSS-REFERENCE TO RELATED APPLICATION

This application claims the benefit of U.S. Provisional Patent Application No. 60/300,250, filed Jun. 21, 2001.

BACKGROUND OF THE INVENTION

1. Field of the Invention

The present invention relates generally to the detection or treatment of cancer, and more specifically, prostate cancer. In particular, an antigen is shown to be associated with prostate cancer, and is useful for new methods and compositions for diagnosing or treating prostate cancer including in individuals with prostate cancer who test negative for Prostate Specific Antigen (PSA).

2. Description of the Related Art

Each year over 300,000 men are diagnosed with prostate cancer in the U.S. alone. It is the most prevalent form of cancer for men of all races. Both the incidence of prostate cancer and its associated mortality have been increasing over the past ten years. It is estimated that about 50–65% of the prostate cancer is localized, 9–17% has spread to an area near the prostate and 20–25% has metastasized to other parts of the body. Screening for prostate cancer is primarily by PSA (a blood test for Prostate Specific Antigen) and DRE (Digital Rectal Exam) testing. Confirmation of cancer is by biopsy. Treatment options depend on disease progression and include surgery, radiation and hormonal manipulation. Chemotherapy has not proven to be successful in the past, but is being tested in combination with other treatments.

As noted above, prostate cancer is currently detected by screening for prostate specific antigen (PSA) and a digital rectal exam (DRE). Neither methodology can differentiate between benign disease and cancer. The failure to differentiate can result, for example, in exposure of patients with benign disease to treatments that are unnecessary and have side effects (e.g., impotency). Moreover, it is estimated that PSA testing misses 20%–30% of all individuals with cancer. There is a clear need for a diagnostic with better sensitivity and specificity.

Furthermore, there is a critical need for therapies that can target prostate cancer cells. Ideally, these types of treatments would have application to both early stage, confined prostate cancer as well as in the treatment of metastatic disease.

In addition, an objective, quantitative measurement of the biochemical target by either demonstrating prostate cancer cell expression and/or measurement in patient specimens would expedite all phases of the therapeutic development, regulatory approval process as well as provide a rationale to stratify patients into more effective treatment groups.

Due to the difficulties in the current approaches to the detection and treatment of prostate cancer, there is a need in the art for improved methods and compositions. The present invention fulfills this need, and further provides other related advantages.

SUMMARY OF THE INVENTION

Briefly stated, the present invention provides for methods and compositions for the detection and treatment of prostate cancer. As used herein, the term "treatment" may include the arrest of tumor growth, the killing of tumor cells, the prevention of tumor cells, the prolongation of survival and may be the result of a B cell and/or T cell response. In one embodiment, a method of screening for prostate cancer in an individual is provided, comprising the step of detecting in a prostate tissue sample, a serum sample, or a urine sample from the individual the presence of an antigen which binds monoclonal antibody NUH2 produced by the cell line having ATCC Deposit No. HB 9762, whereby the presence of the antigen is associated with prostate cancer. In another embodiment, a method is provided for differentiating between benign prostate disease and prostate cancer in a patient diagnosed or presenting with prostate dysfunction, comprising the step of detecting in a prostate tissue sample, a serum sample, or a urine sample from the patient the presence or absence of an antigen which binds monoclonal antibody NUH2 produced by the cell line having ATCC Deposit No. HB 9762, whereby the presence of the antigen is associated with prostate cancer and the absence of the antigen is indicative of benign prostate disease. In another embodiment, a method is provided for eliciting or enhancing, in an individual with increased predisposition to prostate cancer, an immune response to an antigen which binds monoclonal antibody NUH2 produced by the cell line having ATCC Deposit No. HB 9762, comprising the steps of: (a) selecting an individual with increased predisposition to prostate cancer, and (b) immunizing the individual with a composition comprising the antigen and a physiologically acceptable cancer or diluent. In another embodiment, a method is provided for eliciting or enhancing, in a patient suspected to possess prostate cancer cells, an immune response to an antigen which binds monoclonal antibody NUH2 produced by the cell line having ATCC Deposit No. HB 9762, comprising the steps of: (a) selecting a patient suspected to possess prostate cancer cells, and (b) immunizing the patient with a composition comprising the antigen and a physiologically acceptable carrier or diluent. Such immunizations may be repeated one or more times. In another embodiment, a method is provided for killing prostate cancer cells in a patient suspected to possess such cells, comprising the step of delivering an agent, wherein the agent is directly or indirectly cytotoxic, to cells expressing an antigen which binds monoclonal antibody NUH2 produced by the cell line having ATCC Deposit No. HB 9762. In another embodiment, a method is provided for imaging prostate cancer cells in an individual, comprising the steps of: (a) administering to the individual a binding partner for an antigen which binds monoclonal antibody NUH2 produced by the cell line having ATCC Deposit No. HB 9762, and (b) detecting the binding partner in the individual. The present invention provides in a preferred embodiment for the detection or treatment of prostate cancer by the use of monoclonal antibody NUH2 that binds with high specificity to prostate cancer. This and other aspects of the present invention will become evident upon reference to the following detailed description and attached drawings (FIGS. 1–9).

BRIEF DESCRIPTION OF THE DRAWINGS

2f); NCI-H446 (Small cell lung carcinoma (classic)) (FIG. 2g); and Sw1116 (Colon adenocarcinoma) (FIG. 2H).

DETAILED DESCRIPTION OF THE INVENTION

According to the present invention, there exists an antigen that is unexpectedly associated with prostate cancer. A monoclonal antibody (NUH2), previously known for its ability to react with human sperm (U.S. Pat. No. 5,227,160), is shown within the present invention to unexpectedly bind with high specificity to prostate cancer. The murine hybridoma cell line that produces NUH2 has been deposited in American Type Culture Collection (ATCC) and has the ATCC deposit number HB 9762 (U.S. Pat. No. 5,227,160). NUH2 was originally produced from mice injected with the disialyl fraction of gangliosides from human colon cancer. However, as determined in the present disclosure by cell sorting analysis (FACS), this antigen is expressed in relatively low amounts in colon cancer as compared to prostate cancer. Low amounts were also detected in some lung cancer cell lines whereas, all other human cancer cell lines were completely unreactive with NUH2. Surprisingly, however, the antigen is strongly expressed in human prostate cancer cell lines. Cell sorting analysis demonstrates the unexpectedly dramatic expression of this antigen on prostate cancer cells in comparison with all other cancer lines.

As shown by the present disclosure, extensive immunohistology of human tissues with NUH2 demonstrates a high specificity to prostate adenocarcinoma. The antigen was also found on a very limited number of normal tissues, i.e., sperm, placenta, a few scattered cells in tonsil and a single cell layer of cell lining the glandular epithelium of the prostate. However, none of these normal tissues is crucial to patients with prostate cancer. All other normal tissues were completely devoid of this antigen. This distribution allows such marker to be an excellent candidate not only as a diagnostic target, but also as a target for therapy of prostate cancer.

The antigen detected by antibody NUH2 is the disialylated carbohydrate known as sialyl I which has the following structure:

Sialyl I is found on sperm, and many anti-sperm antibodies detected as a cause for infertility in certain men and women bind sialyl I and its derivatives. The expression of these antibodies in infertile patients allows a source of human B cells to develop strictly human antibodies specific for sialyl I as agents for the immunotherapy of patients with prostate cancer.

Antibody NUH2 binds strongly to the disialylganglioside containing the sialyl I purified from prostate cancer cells as determined by direct binding in an ELISA format. Binding is completely destroyed by treatment of immobilized disialylganglioside with neuraminidase which cleaves the terminal sialic acid residues. Although the terminal sialic acid residues are required, the shorter monosialylganglioside GM3 that contains the same terminal carbohydrate sequence shown below was completely unreactive:

Interestingly, the same terminal carbohydrate sequence in GM3 shown above (3'sialyllactose) chemically linked to a protein carrier (serum albumin) was able to bind antibody NUH2. This suggests that the correct density and orientation of this terminal carbohydrate sequence are critical for binding to antibody NUH2. This synthetic glycoconjugate antigen, 3'sialyllactose-serum albumin, can be used as a basis to optimize synthetic antigens for NUH2 by varying the valency, length, and density of the carbohydrate structures containing the 3'sialyllactose epitope. Other backbone carriers, such as polyacrylamide, augment this synthetic approach.

For diagnostic purposes, a prostate tissue sample may be taken from an individual and tested for the presence of the antigen that binds antibody NUH2. It will be appreciated by one of ordinary skill in the art that a prostate tissue sample can be tested for the antigen in a variety of ways, including by immunohistological and non-immunological means. The tissue sample can exclude the single cell layer of cell lining the glandular epithelium, or include cells both within and outside the layer. The prostate tissue sample may be the result of a biopsy procedure. The prostate tissue sample may be a plurality of contiguous cells and/or one or more separate cells from the prostate.

Sialyl I is present in both glycolipids and glycoproteins in prostate cancer cells, and in the prostate cancer cell line, DU145, the sialyl I antigen is shed into the culture media. Purification of the secreted sialyl I glycoprotein from DU145 cells demonstrates the presence of this epitope in large mucin-like glycoproteins with very high molecular weights. The discovery of this shed form of the antigen allows for another diagnostic assay for prostate cancer. Because the antigen is shed by prostate cancer cells, a diagnostic assay need not be restricted to prostate tissue samples. Sources of shed antigen include body fluids, such as patient blood or urine samples. As used herein, detecting the presence of the antigen includes detecting prostate cancer cells possessing the antigen, or the antigen independent of the cells, or both. Preferred samples for diagnostic screening are a prostate tissue sample, a serum sample and a urine sample.

The large shed glycoprotein antigen from human prostate cancer cell line DU145 was purified and used to develop a diagnostic assay based on a sandwich ELISA format of NUH2 antibodies. Using such glycoprotein antigen as a standard, the assay has a dynamic range over several orders of magnitude and a sensitivity to detect nanogram amounts of antigen based on carbohydrate content.

Tests for prostate specific antigen (PSA) are well known in the art. As noted above, screening for PSA to detect prostate cancer is estimated to miss (i.e., false negatives) a significant proportion of the individuals tested who actually have prostate cancer. An advantage of the present invention is that the method of screening for prostate cancer may detect prostate cancer in an individual having the cancer but who tests negative in a test for PSA. The present method may be used alone or in combination with a test for PSA.

As noted above, the current approaches to screening for prostate cancer are unable to differentiate between benign prostate disease and prostate cancer. For therapy purposes, it is important to be able to determine whether a patient diagnosed or presenting with prostate dysfunction has a benign prostate disease or prostate cancer. Benign prostate disease includes benign prostatic hyperplasia (BPH). Another advantage of the present invention is that by detecting for antigen which binds antibody NUH2, prostate cancer may be distinguished from benign prostate disease in a patient diagnosed or presenting with prostate dysfunction. The presence of antigen is associated with prostate cancer. The absence of antigen is indicative of benign prostate disease. A patient diagnosed or presenting with prostate dysfunction may have been tested in a test for PSA, and may have tested negative.

It may be desirable to elicit or enhance an immune response to the antigen on prostate cancer cells that binds antibody NUH2. The immune response may be a T cell or B cell response. The immune response may be elicited for the first time in a warm-blooded animal, such as a human. Alternatively, it may be enhanced in an organism where a response is present but at insufficient levels. In one embodiment, an individual is selected based on an increased predisposition to prostate cancer. The increased predisposition may be based, for example, upon age, family history or ethnicity. The individual selected is immunized with a composition comprising the antigen and a physiologically acceptable carrier or diluent. Antigen may be coupled to an appropriate immunogenic carrier, such as keyhole limpet hemocyanin (KLH), to include in a composition to elicit or enhance an immune response. Immunizing with the antigen which binds antibody NUH2 in a composition includes immunizing with the naturally occurring antigen or truncated versions, or synthetic versions (chemical or recombinant) or variations of either. Sources of antigen for immunization include human placenta or DU145 cells. Antigen may be coated on *Salmonella minnesotae* (commercially available as the adjuvant Detox).

In another embodiment of immunizing, a patient is selected who is suspected to possess prostate cancer cells. For example, the patient may be selected based upon a positive result in a screening method, such as that described herein or for PSA. The individual selected is immunized with the composition described above. Immunization may be performed on the patient in combination with other procedures.

Sialyl I carbohydrate structures are also found in disialogangliosides and glycoproteins in human placenta. This is an adequate source of antigenic material for the development of humanized antibodies directed against the sialyl I carbohydrate structure for the diagnostic imaging or immunotherapy of prostate cancer patients. In addition, antibodies or other agents that bind to the antigen can be covalently or noncovalently bound to, or fusion constructs prepared from, a molecule that is directly or indirectly cytotoxic to prostate cancer cells, using methodology well known to those of ordinary skill in the art. The cytotoxic molecule may be directly cytotoxic to prostate cancer cells without the necessity for activation, or may be indirectly cytotoxic by requiring activation in vivo (e.g., by the presence or administration of an activating molecule) including as a prodrug, or itself activating in vivo another molecule(s) which is then cytotoxic to prostate cancer cells (e.g., complement mediated cell lysis). Treatment of prostate cancer may result, for example, in remission of the cancer or prolongation of survival time.

In an embodiment of the present invention, a method is provided for killing prostate cancer cells in a patient suspected to possess such cells. An agent which is directly or indirectly cytotoxic is delivered to prostate cancer cells. The agent may be delivered by attachment (e.g., covalent, non-covalent or fusion construct) to a binding partner for the antigen which binds monoclonal antibody NUH2 produced by the cell line having ATCC Deposit No. HB 9762. The binding partner may be an antibody, such as NUH2, or a nonantibody molecule that binds to the antigen (e.g., a lectin or small organic molecule). Suitable agents include therapeutic radioisotopes, chemotherapeutic compounds and cytotoxic prodrugs. Alternatively, the agent delivered to prostatic cancer cells is not attached to the binding partner for the antigen. For example, numerous pretargeting methodologies are well known in the art (e.g., U.S. Pat. No. 4,863,713 to Goodwin et al. and subsequent improvements by others) wherein the binding partner for a molecule on a cell is delivered to the cell prior to the introduction of the cytotoxic agent. Generally, a ligand/anti-ligand pair is utilized wherein the ligand is attached to the binding partner, and the anti-ligand is attached to the cytotoxic agent. A typical ligand/anti-ligand pair is avidin (or streptavidin) and biotin. Pretargeting methodologies are generally used in a two or three step process, and may additionally include a clearing agent other than anti-ligand to remove binding partner-ligand not bound to prostate cancer cells. The method of the present invention for killing prostate cancer cells may be used in combination with other cancer therapies (e.g., surgery, radiation, chemotherapy and immunotherapy).

In another embodiment of the present invention, a method is provided for imaging prostate cancer cells in an individual. A binding partner, as described above, for the antigen is administered to the individual in an amount sufficient to image prostate cancer cells. As noted above, prostate cancer cells may be localized to the prostate and/or migrated from the prostate to another location in the body. It is important to detect prostate cancer cells that have migrated from the prostate as this will likely influence the treatment regime for the individual. The binding partner administered will associate with the antigen (i.e., the antigen on the prostate cancer cells). The binding partner bound to the prostate cancer cells may be detected in a variety of ways, such as by direct or indirect means. In direct means, the binding partner possesses a detectable component, such as a radioisotope. In indirect means, the binding partner does not possess a detectable component. Instead, a molecule which possesses a detectable component and binds to the binding partner (or a combination of molecules, such as a ligand/anti-ligand pair wherein one member binds to the binding partner and the other member possesses a detectable component) may be administered subsequent to the binding partner. The method may be performed using a pretargeting format, as described above.

Antigen or antigen binding partner (either referred to as compound) of the present invention may be administered in a manner appropriate for diagnosis or therapy. Appropriate dosages and a suitable duration and frequency of administration may be determined by such factors as the condition of the patient, the type and severity of the patient's disease and the method of administration. In general, an appropriate dosage and regimen provides the compound in an amount sufficient to provide diagnostic, therapeutic and/or prophylactic benefit. Within particularly preferred embodiments of the invention, a compound may be administered at a dosage ranging from 0.001 to 100 mg/kg body weight. Appropriate dosages may generally be determined using experimental models and/or clinical trials. In general, the use of the minimum dosage that is sufficient to provide effective diagnosis or therapy is preferred. Patients may generally be monitored for therapeutic effectiveness using assays suitable for the condition being treated or prevented, which will be familiar to those of ordinary skill in the art.

The following examples are offered by way of illustration and not by way of limitation.

EXAMPLES

Example 1

Immunohistology of Sections of Human Tissues

Figure 1:
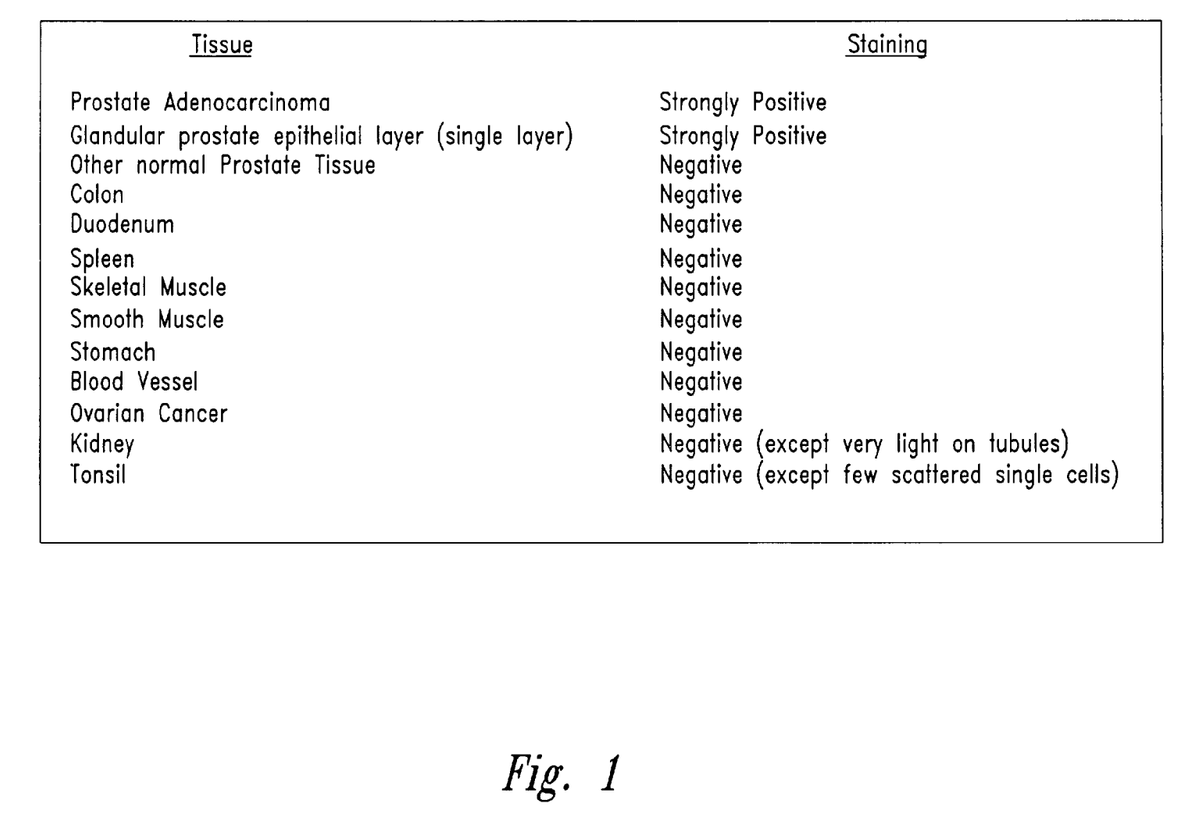
FIG. 1 is a table that summarizes the immunohistology of human tissue sections using antibody NUH2.
Figure 2A:
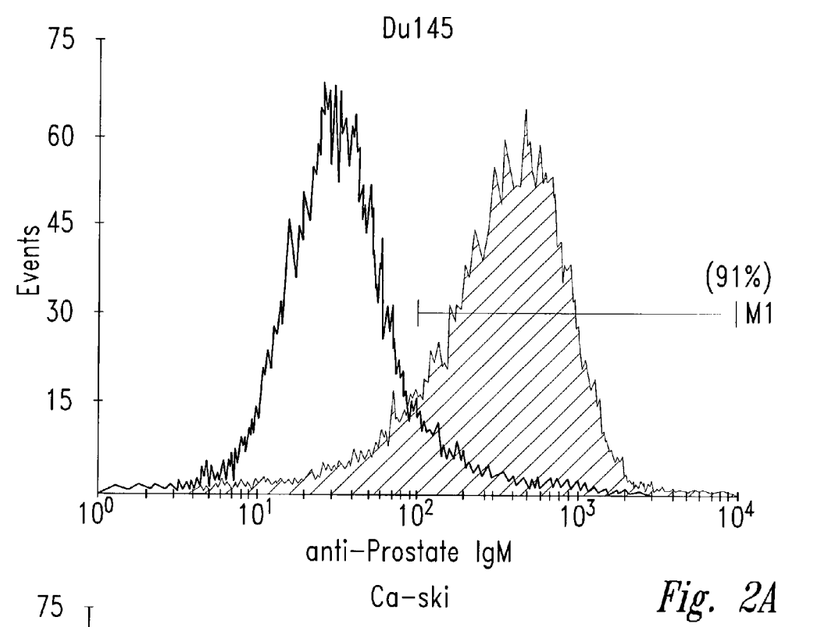
FIGS. 2a–h shows superimposed histograms of cell sorter analysis. Each cell line is reacted with NUH-2 antibody (shaded) or control IgM (open). The cell lines are the following: Du-145 (Prostate adenocarcinoma) (FIG. 2a); Ca-ski (Cervical Carcinoma) (FIG. 2b); KG1-a (Acute myelogenous leukemia) (FIG. 2c); NCI-H82 (Small cell lung carcinoma (variant)) (FIG. 2d); C-33a (Cervical adenocarcinoma) (FIG. 2e); A431 (Epidermoid carcinoma) (FIG.
Figure 2B:
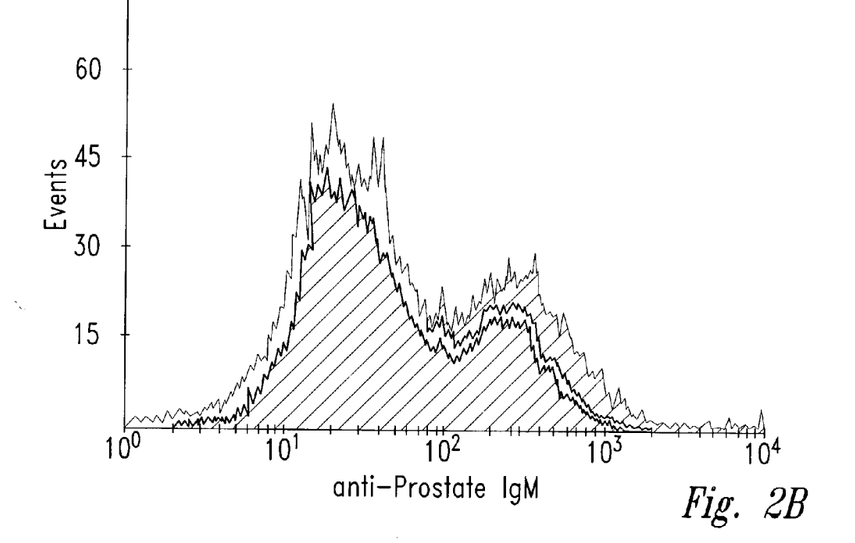
Figure 2C:
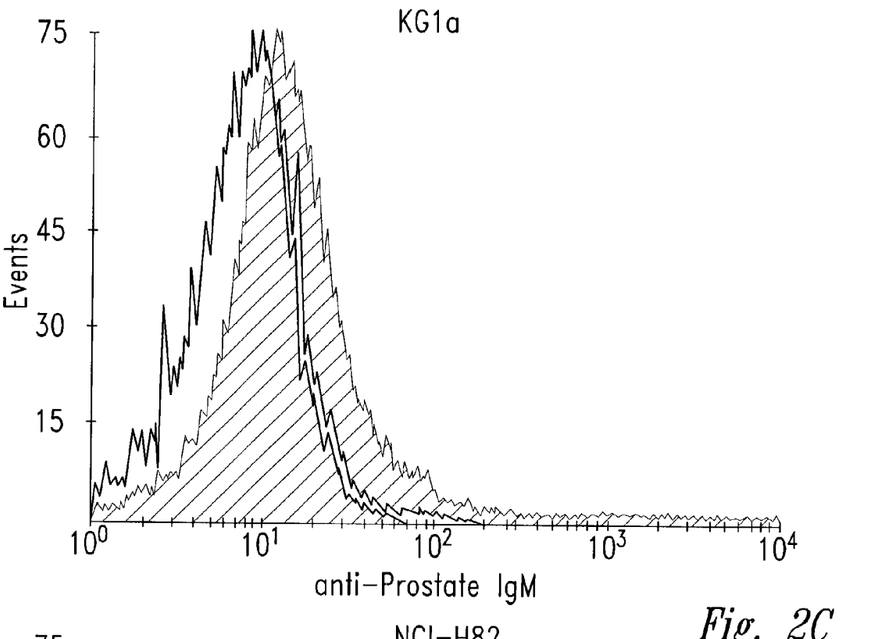
Figure 2D:
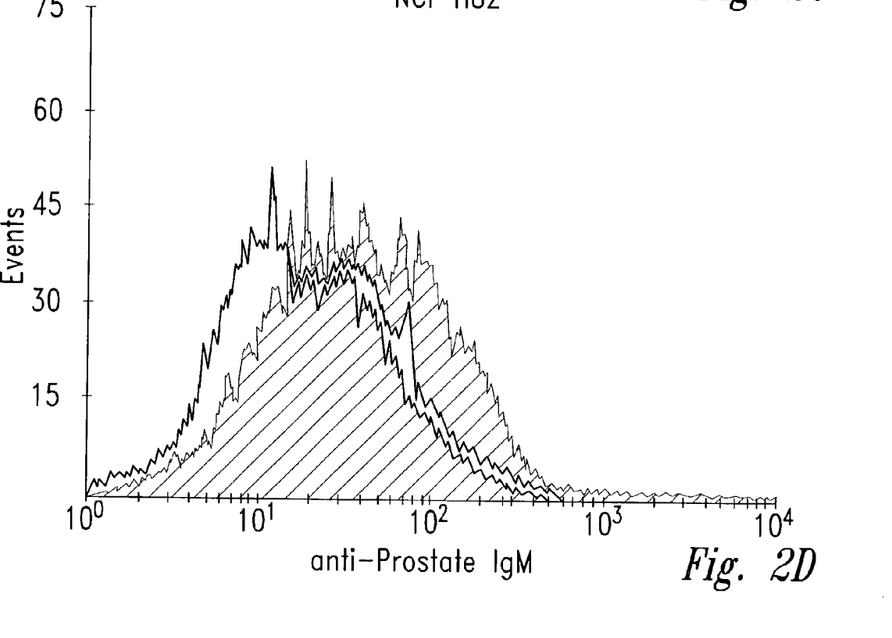
Figure 2E:
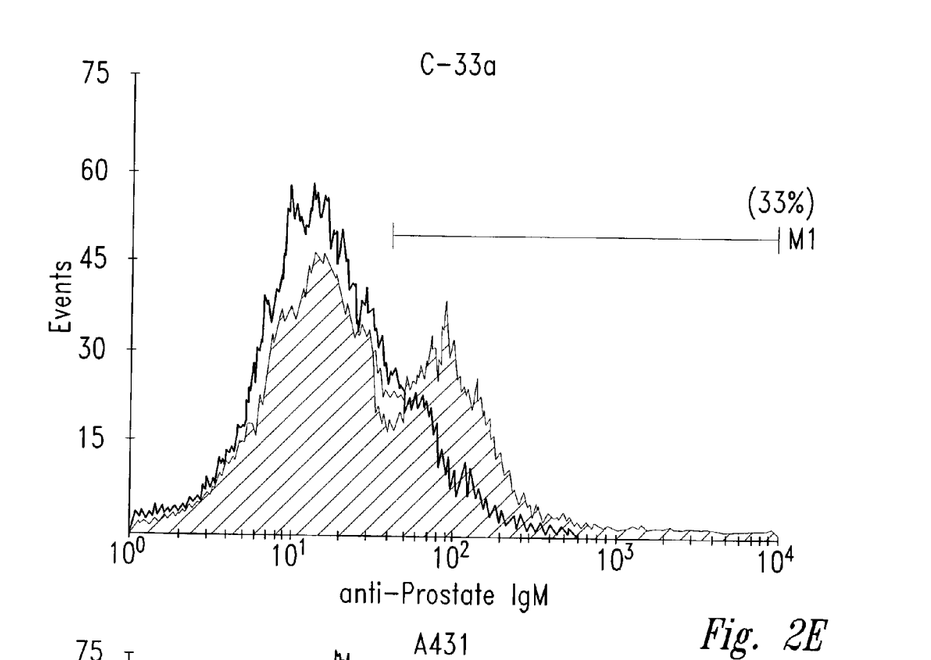
Figure 2F:
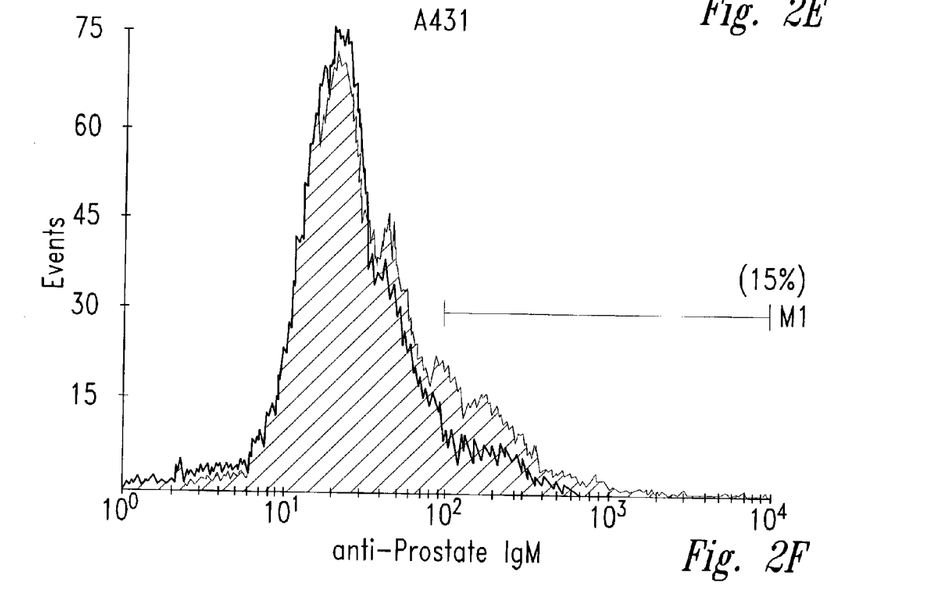
Figure 2G:
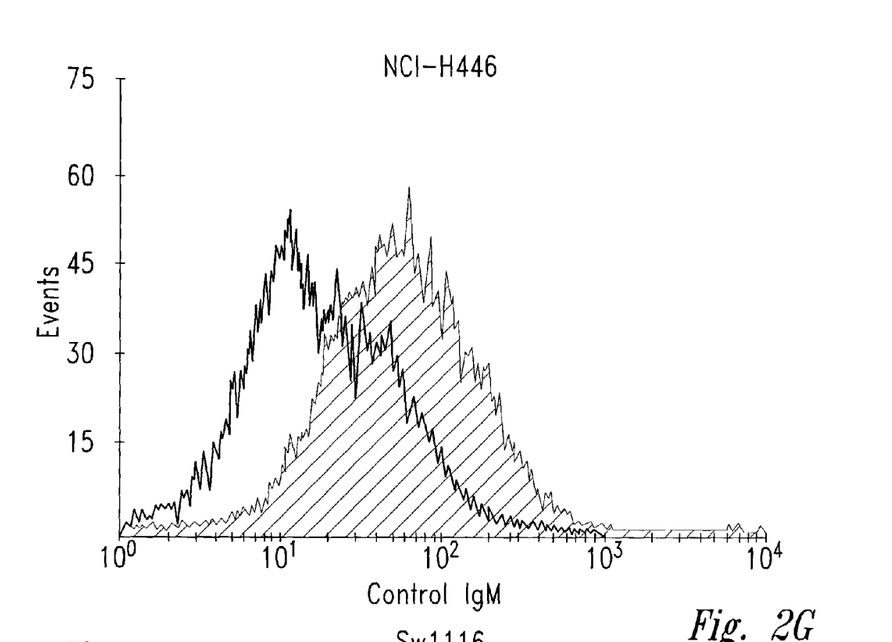
Figure 2H:
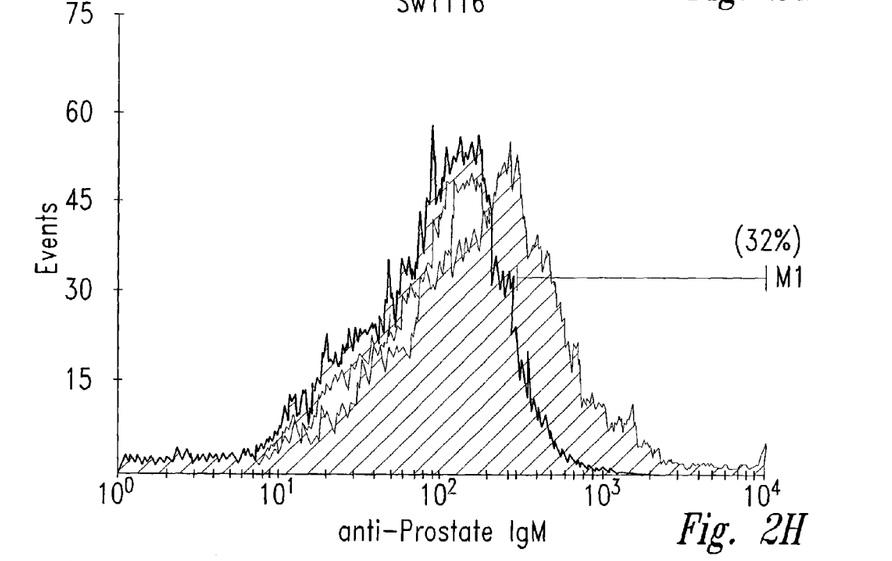

Tissue sections obtained from various human organs were directly stained with antibody NUH2. A second anti-IgM antibody chemically linked to horseradish peroxidase (HRP) further reacted with the tissue section and the location of bound antibody was observed by reaction with the FW substrate. Tissues sections were counter stained with eosin to detect location of cells in the section by a blue color. As shown in FIG. 1 most normal tissues were completely negative and did not bind antibody NUH2. Prostate adenocarcinoma, however, strongly bound NUH2 and strongly expresses the antigen, sialyl I. Normal prostate showed expression of antigen restricted to one single cell layer lining the glandular epithelium. All other cells in normal prostate were negative. This antigen is highly restricted to prostate cancer and is negative for most normal tissues tested. Over 95% of tonsil was negative, however, several scattered single cells within the outer edges of the tonsil were positive.

Example 2

Expression of Prostate Cancer Antigen (Sialyl I) on Tumor Cell Lines as Determined by Cell Sorting Using Antibody NUH2

Human tumor cell lines were washed with phosphate-buffered saline (PBS) and allowed to bind to antibody NUH2 in suspension at a concentration of 10 µg/ml in PBS. A duplicate sample of the same cell line was incubated with a control IgM murine antibody in parallel as a negative control. After incubation for 1 hour at 4° C., the cells were washed with PBS and incubated with goat anti-mouse IgM coupled to FITC. The intensity of fluorescence was measured for each population by fluorescence activated cell sorter analysis (FACS). For direct visualization of the results, histograms of the same cell type reacted with either NUH2 or control antibody were superimposed (FIG. 2). Prostate cancer cell line DU145 strongly expresses sialyl I antigen, whereas most other tumor cell lines were completely negative. The lung cancer cell line NCIH446 and the colon cancer cell line SWI 116 displayed some weak expression.

Figure 3:
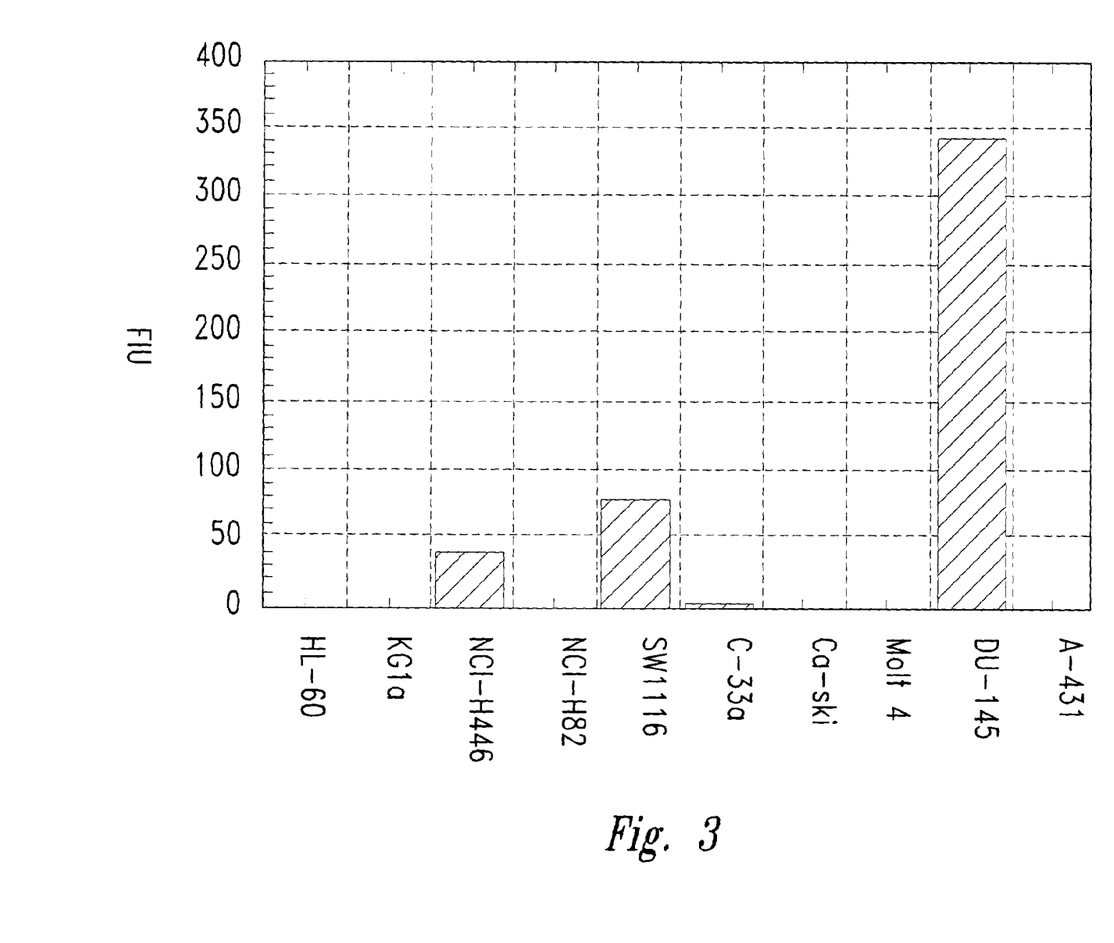
FIG. 3 is a tabulation of the immunostaining of cancer cell lines with NUH2 antibody.

The results of the immunostaining of cancer cell lines with NUH2 antibody are shown in FIG. 3 and the table below.

| Cell Line | Cancer | Cell Surface Reactivity |
|---|---|---|
| 1. HL60 | Promyelocytic leukemia | Negative |
| 2. KG1a | Acute myelogenous leukemia | Negative |
| 3. NCI-H446 | Small cell lung carcinoma (classic) | 40 FIU |
| 4. NCI-H82 | Small cell lung carcinoma (variant) | Negative |
| 5. SW1116 | Colon adenocarcinoma | 79 FIU |
| 6. C-33a | Cervical adenocarcinoma | 4 FIU |
| 7. Ca-ski | Cervical carcinoma | Negative |
| 8. Molt 4 | Acute lymphoblatic leukemia (T cell) | Negative |
| 9. Du-145 | Prostate adenocarcinoma | 345 FIU |
| 10. A-431 | Epidermoid carcinoma | Negative |
| 11. MCF-7 | Breast carcinoma | Negative |

Example 3

Immunostaining Glycolipid Antigens Directly on Thin Layer Chromatograms Using Antibody NUH2

Glycolipids were extracted from tissues using chloroform and methanol according to the Folch procedure and separated into aqueous (upper) and organic (lower) phases. The upper phase extract was dried under rotary evaporation and the glycolipids were resuspended in methanol and subjected to ion exchange chromatography using DEAE Sepharose®. Neutral glycolipids elute in the non-bound fractions while charged glycolipids were eluted with increasing concentrations of ammonium bicarbonate in methanol.

Figure 4:
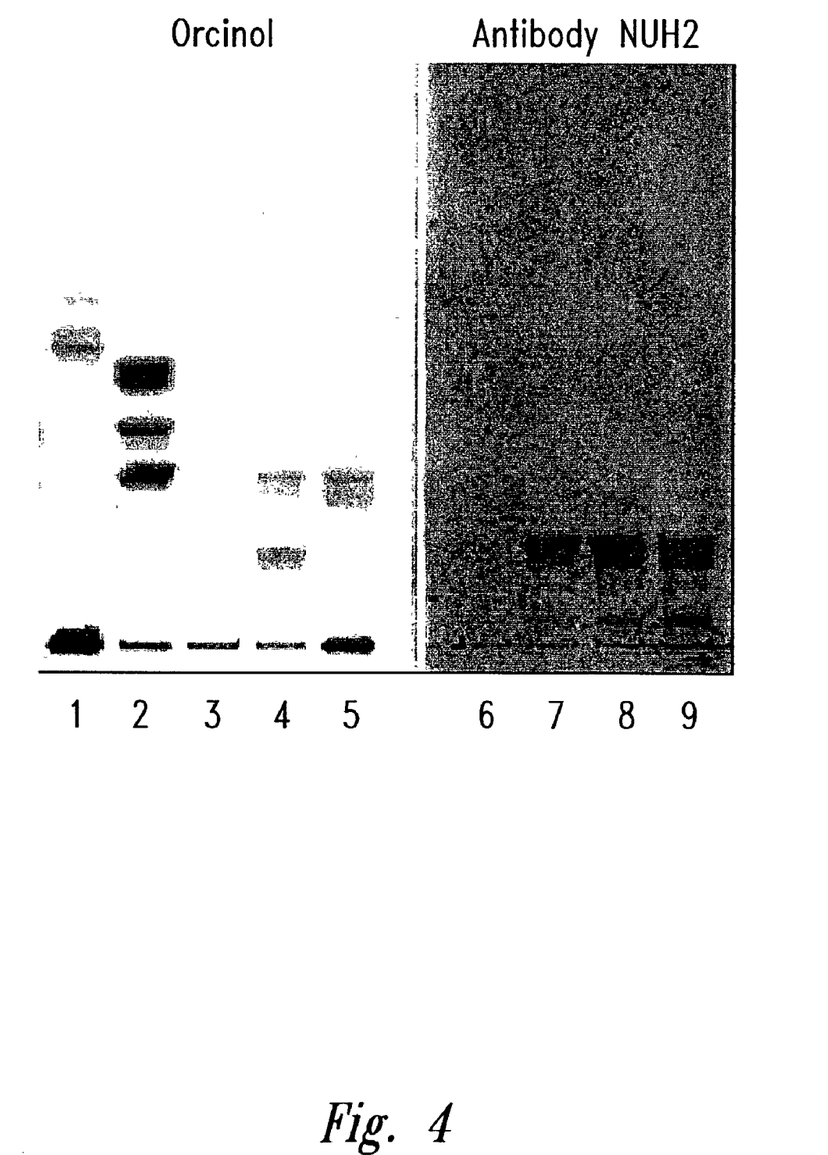
FIG. 4 shows the staining of glycolipids directly on thin layer chromatograms. The left panel (lanes 1–5) was orcinol staining (carbohydrate staining). The right panel (lanes 6–9) was immunostaining with NUH2 antibody. Lanes 1 to 5: 1 Neutral glycolipids from human placenta, 2 monosialylgangliosides from human placenta, 3 sulfatides from human placenta, 4 disialylgangliosides from human placenta, 5 disialylgangliosides from bovine red blood cells. Lanes 6 to 9: 6 monosialylgangliosides from human placenta, 7 to 9 2-fold increasing concentrations of disialylgangliosides from human placenta.

Samples from various fractions were applied to a silica gel high performance thin layer chromatography plate (HPTLC) and the chromatograms were developed in a chamber containing chloroform/methanol/0.02%$CaCl_2$ (5:4:1). After chromatography, the dried plate was cut into sections for chemical staining and immunostaining. Orcinol reagent was used to chemically stain a section of the plate to detect all glycolipids. Immunostaining the other section of the plate with antibody NUH2 revealed the migration (Rf), number and relative prevalence of glycolipid antigens of NUH2 containing the epitope in sialyl I (FIG. 4).

Briefly, immunostaining was conducted by first coating the plate with polyisobutylmethacryate following by incubation in Tris buffered saline (TBS) containing 2% BSA for 2 hours. Plates were then washed in TBS and incubated with antibody NUH2 in TBS (10 µg/ml) containing 1% BSA. After 1 hour, the plate is washed in TBS and incubated with horseradish peroxidase (HRP) labeled goat anti-mouse IgM in TBS (1 µg/ml) containing 1% BSA. After 1 hour, the plate is washed and incubated with TMB reagents. To quench the substrate reaction with the HRP, the plate is washed in water and allowed to air dry. Glycolipid antigens of antibody NUH2 displayed a dark blue color.

Example 4

Figure 5:
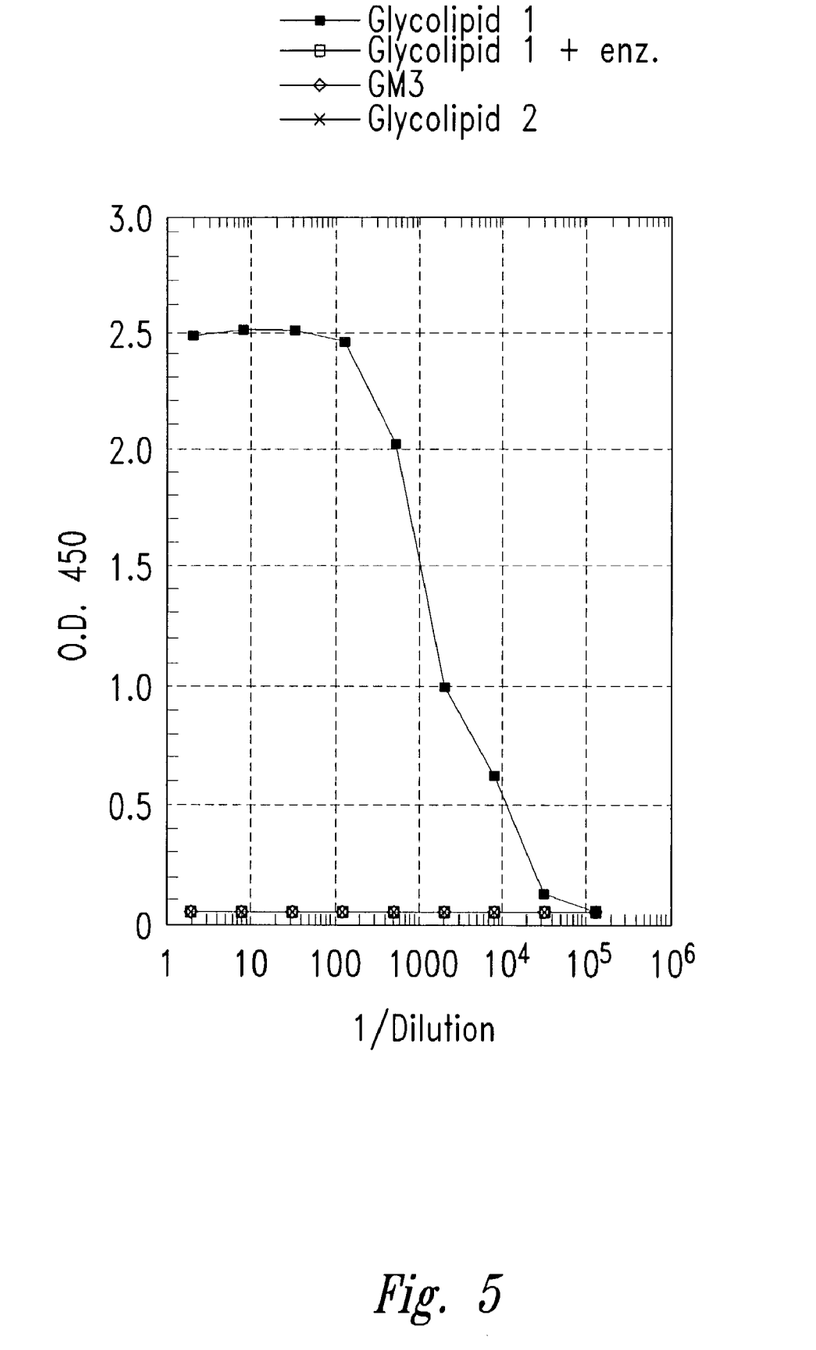
FIG. 5 depicts the binding of antibody NUH2 to gangliosides immobilized on solid phase.

Direct Binding of Antibody NUH2 to Purified Glycolipid Antigens Immobilized on Solid Phase Glycolipids were coated in 96 well plates and reacted with antibody NUH2 in an ELISA-type format (FIG. 5). Briefly, glycolipids dissolved in methanol were placed in the wells of a microliter plate and the plate was allowed to dry under vacuum. Wells were then incubated with 1% BSA in TBS to block non-specific binding. After washing with TBS, wells were then incubated with antibody NUH2 diluted in TBS, 1% BSA at 10 µg/ml. After incubation for 1 hour, the wells were washed with TBS and incubated with HRP-labeled goat anti-mouse IgM diluted in TBS, 1% BSA at 1 µg/ml. After 1 hour incubation, the wells were washed with TBS and incubated with TMB reagent for 10 minutes. Reaction was then quenched with 1M phosphoric acid and the optical density of the wells was determined at a wavelength of 450 nm.

Example 5

Figure 6:
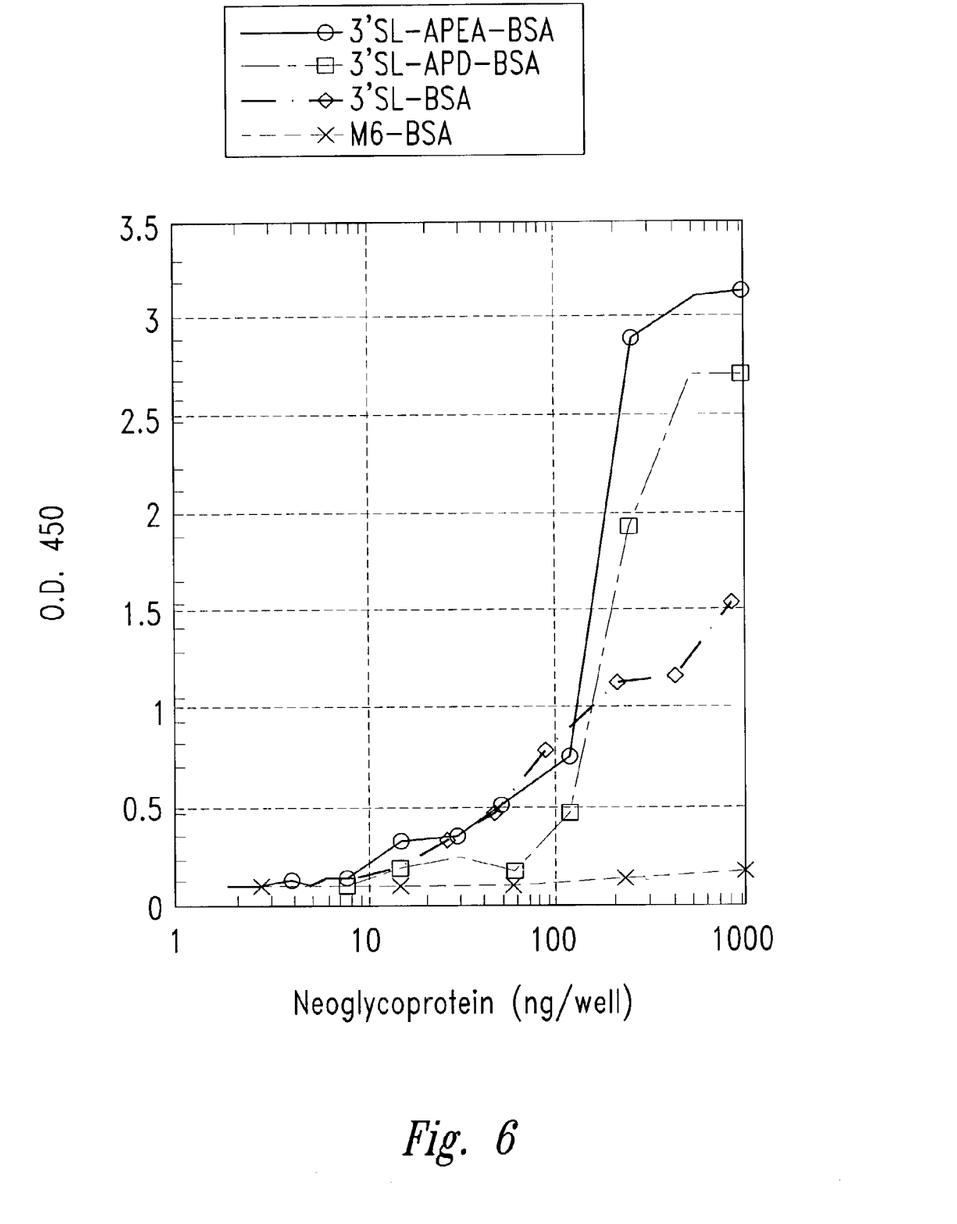
FIG. 6 shows the binding of antibody NUH2 to synthetic neoglycoproteins immobilized on solid phase.

Direct Binding of Antibody NUH2 to Synthetic Neoglycoproteins Immobilized on Solid Phase Synthetic neoglycoproteins were produced by chemically linking purified carbohydrate structures to either bovine or human serum albumin through either APD or APE spacers. Approximately 10 to 15 carbohydrates were linked to each albumin molecule. Neoglycoproteins were then coated in the wells of a microliter plate and reacted with antibody NUH2 in an ELISA-type format (FIG. 6). Briefly, neoglycoproteins diluted in TBS were incubated in the wells of a microliter plate at 4° C. overnight. Wells were then washed with TBS and incubated with 1% BSA in TBS to block non-specific binding. After washing with TBS, wells were then incubated with antibody NUH2 diluted in TBS, 1% BSA at 10 µg/ml. After incubation for 1 hour, the wells were washed with TBS and incubated with HRP-labeled goat anti-mouse IgM diluted in TBS, 1% BSA at 10 µg/ml. After 1 hour incubation, the wells were washed with TBS and incubated with TMB reagent for 10 minutes. Reaction was then quenched with 1M phosphoric acid and the optical density of the wells was determined at a wavelength of 450 nm.

Example 6

Purification of Large Glycoproteins Antigens Containing the Sialyl I Epitope Secreted from the Prostate Cancer Cell Line DU145.

Figure 7:
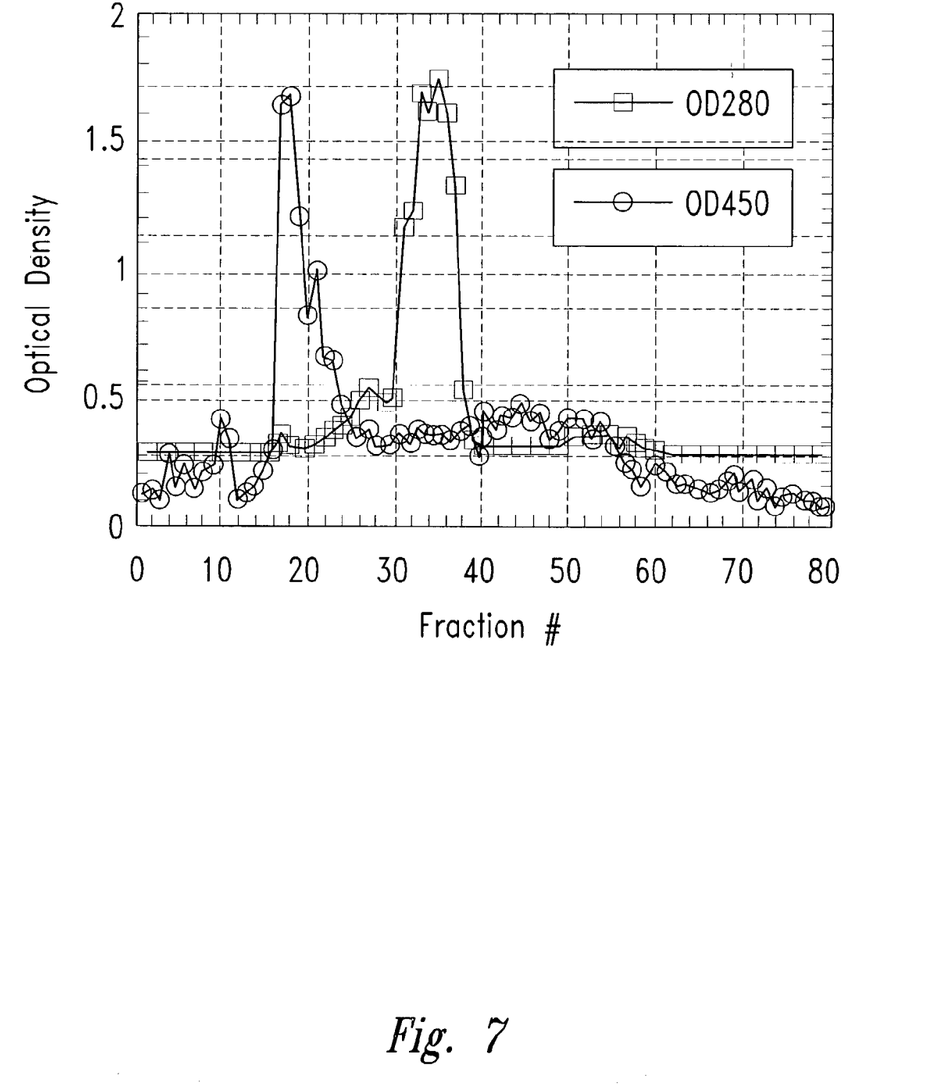
FIG. 7 illustrates the purification by Sephacryl S-400 chromatography of large glycoprotein shed from prostate cancer cell line.

Glycoprotein antigens shed into tissue culture supernatant by human prostate cancer cell line DU145 were purified by chromatography using Sephacryl® S400 (FIG. 7). Briefly, tissue culture supernatant was concentrated 10 fold by membrane filtration. Aliquots of 10 ml were applied to a column of Sephacryl® S400 equilibrated in phosphate buffered saline (PBS). Fractions were collected and analyzed for antigenic activity by the diagnostic assay described in Example 7. Most of the reactivity eluted in void volume, which is consistent with typical large molecular weight mucin tumor markers.

Example 7

Development of a Diagnostic Assay for Prostate Cancer

Figure 8:
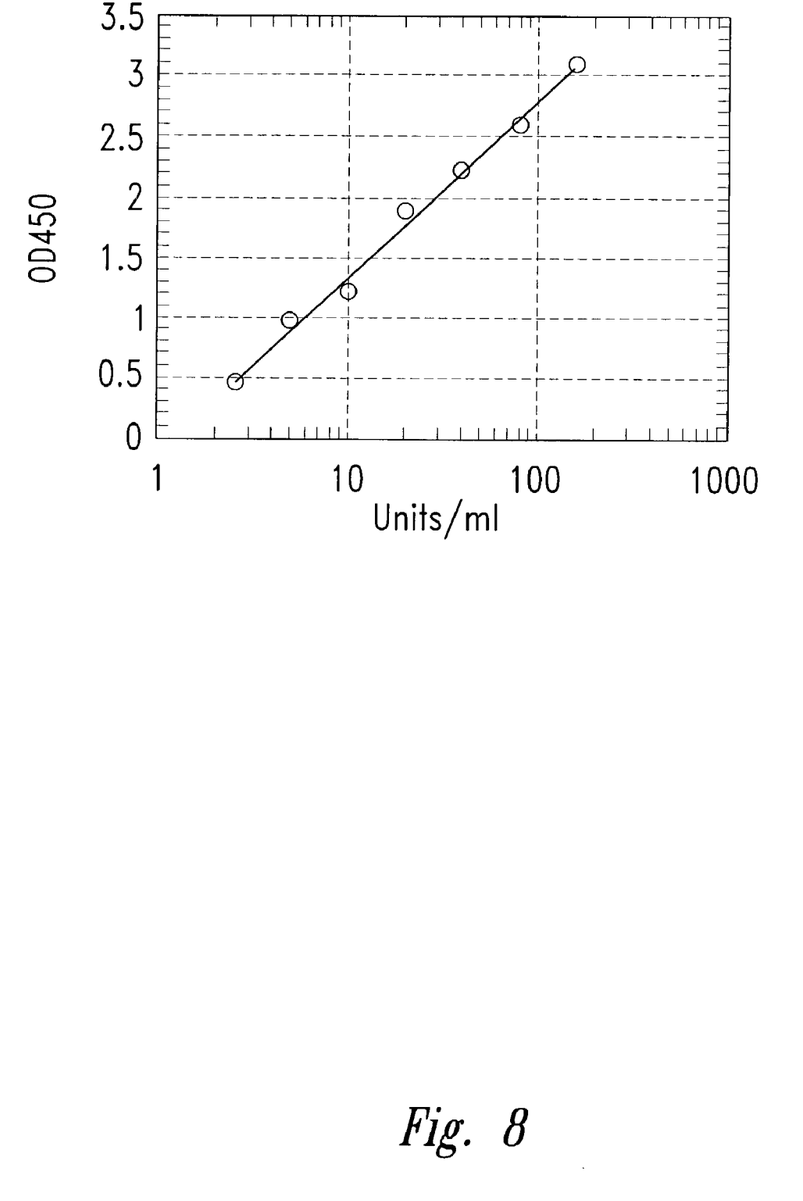
FIG. 8 depicts a standard binding curve for a prostate cancer diagnostic assay using antibody NUH2 and shed prostate cancer glycoprotein.
Figure 9:
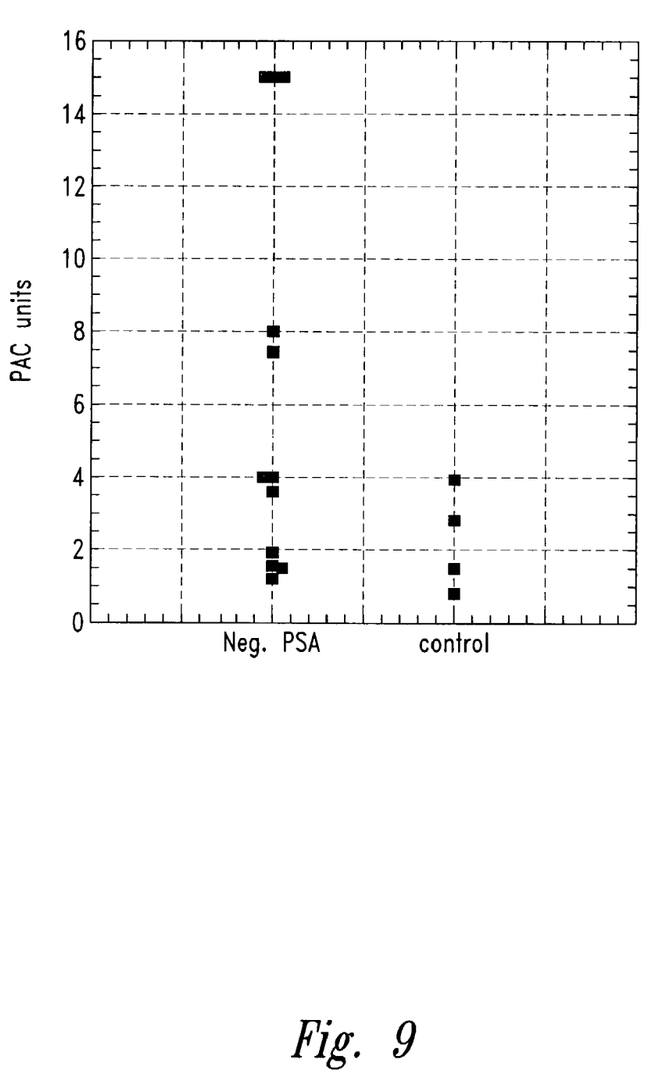
FIG. 9 shows an assay of the present invention can detect prostate cancer in individuals that are missed by the PSA assay.

A diagnostic assay was developed using antibody NUH2 in a sandwich ELISA format (FIGS. 8 and 9). The glycoprotein antigen shed by DU145 cells and purified as described in Example 6, was used as a standard for the assay. NUH2 was coupled to horseradish peroxidase (HRP) by treating the enzyme with periodate and reacting the oxidized molecule with antibody NUH2 thereby creating the conjugate, NUH2-HRP.

Briefly, for the assay, wells of a microliter plate were coated with antibody NUH2 and subsequently blocked by incubation with PBS (containing 1% BSA) mixed 1:1 (v/v) with blocking buffer (StabilCoat, purchased from SurModics, Inc., Eden Prairie, Minn.). Wells were washed with PBS and incubated with test sample (e.g., sera) and other wells with glycoprotein standards. After incubation, the wells were washed with PBS and incubated with NUH2-HRP in blocking buffer. After incubation, wells were washed then incubated with TMB reagent for 10 minutes at room temperature. Reaction was then quenched with 1M phosphoric acid and the optical density of the wells was determined at the wavelength of 450 nm.

Sera from normal and PSA negative males were tested for the presence of antigen using this diagnostic assay. In all cases, sera were tested after 10-fold dilution in PBS (20 mM phosphate, 0.15 M NaCl, pH 7.0). Sera from prostate cancer patients that were negative from the PSA marker as determined by the Abbott IMx assay (Neg. PSA) were purchased from IMPATH-BCP, Inc., Franklin, Mass. Sera donated from normal healthy males under the age of 50 were used as a control group. As shown in FIG. 9, the present assay detected prostate cancer in patients that are missed by the PSA assay.

From the foregoing, it will be evident that, although specific embodiments of the invention have been described herein for purposes of illustration, various modifications may be made without deviating from the spirit and scope of the invention.

The invention claimed is:

1. A method of screening for prostate cancer in an individual, comprising the step of detecting in a prostate tissue sample from the individual the presence of an antigen which binds monoclonal antibody NUH2 produced by the cell line having ATCC Deposit No. HB 9762, whereby the presence of the antigen is associated with prostate cancer, and wherein the antigen comprises the structure:

2. The method of claim 1 wherein the individual tests negative in a test for prostate specific antigen (PSA).

* * * * *